US012778407B2

(12) United States Patent
Jeon et al.

(10) Patent No.: US 12,778,407 B2
(45) Date of Patent: Nov. 3, 2026

(54) INTRAORAL SCANNER

(71) Applicant: ARCREAL INC., Seoul (KR)

(72) Inventors: Seung Hyun Jeon, Seoul (KR); Kyong Kook Kim, Seoul (KR)

(73) Assignee: ARCREAL INC., Seoul (KR)

( * ) Notice: Subject to any disclaimer, the term of this patent is extended or adjusted under 35 U.S.C. 154(b) by 276 days.

(21) Appl. No.: 18/705,705

(22) PCT Filed: Oct. 31, 2022

(86) PCT No.: PCT/KR2022/016824
§ 371 (c)(1),
(2) Date: Apr. 29, 2024

(87) PCT Pub. No.: WO2023/075547
PCT Pub. Date: May 4, 2023

(65) Prior Publication Data

US 2026/0123830 A1 May 7, 2026

(30) Foreign Application Priority Data

Oct. 29, 2021 (KR) ........................ 10-2021-0146626
Oct. 28, 2022 (KR) ........................ 10-2022-0141641

(51) Int. Cl.
*A61B 1/247* (2006.01)
*A61B 1/00* (2006.01)

(52) U.S. Cl.
CPC .......... *A61B 1/247* (2013.01); *A61B 1/00194* (2022.02)

(58) Field of Classification Search
CPC ............................ A61B 1/247; A61B 1/00194
USPC ............................................................ 348/66
See application file for complete search history.

(56) References Cited

U.S. PATENT DOCUMENTS

2013/0236850 A1 9/2013 Wu et al.
2014/0248576 A1* 9/2014 Tchouprakov ....... A61C 9/0073 433/29
2014/0272775 A1 9/2014 Monty
2019/0247163 A1 8/2019 Wu et al.
(Continued)

FOREIGN PATENT DOCUMENTS

KR 10-1533341 B1 7/2015
KR 10-1611415 B1 4/2016
KR 10-2016-0133112 A 11/2016
(Continued)

OTHER PUBLICATIONS

International Search Report for PCT/KR2022/016824 mailed on Feb. 13, 2023.

(Continued)

*Primary Examiner* — Nguyen T Truong
(74) *Attorney, Agent, or Firm* — The PL Law Group, PLLC

(57) ABSTRACT

An intraoral scanner according to an embodiment includes a case having an opening part formed at one end thereof, a light source part disposed inside the case and configured to emit light, a first optical system disposed at the opening part and configured to reflect the light emitted from the light source part toward a subject located outside the case, a second optical system disposed adjacent to the first optical system and configured to reflect light reflected from the subject toward the inside of the case, and an image sensor part configured to detect the light reflected by the second optical system.

9 Claims, 3 Drawing Sheets

(56) References Cited

U.S. PATENT DOCUMENTS

2020/0205942 A1 7/2020 Pesach et al.

FOREIGN PATENT DOCUMENTS

| | | | |
|---|---|---|---|
| KR | 10-2018-0024477 | A | 3/2018 |
| KR | 10-1874547 | B1 | 7/2018 |
| KR | 10-2341890 | B1 | 12/2021 |
| WO | WO 2014/144434 | A1 | 9/2014 |

OTHER PUBLICATIONS

European Search Report for EP 22887741.1 issued on Jan. 9, 2025 from European patent office in a counterpart European patent application.

Office action issued on Jul. 11, 2024 from Korean Patent Office in a counterpart Korean Patent Application No. 10-2022-0141641 (English translation is also submitted herewith. ).

Office action issued on Mar. 12, 2025 from Korean Patent Office in a counterpart Korean Patent Application No. 10-2022-0141641 (English translation is also submitted herewith.).

Office action issued on Nov. 19, 2025 from Korean Patent Office in a counterpart Korean Patent Application No. 10-2022-0141641 (English translation is also submitted herewith.).

Notice of allowance issued on Apr. 20, 2026 from Korean Patent Office in a counterpart Korean Patent Application No. 10-2022-0141641 (English translation is also submitted herewith.).

* cited by examiner

INTRAORAL SCANNER

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2022/016824 filed on Oct. 31, 2022, which claims priority to the benefit of Korean Patent Application Nos. 10-2021-0146626 filed on Oct. 29, 2021 and 10-2022-0141641 filed on Oct. 28, 2022 in the Korean Intellectual Property Office, the entire contents of which are incorporated herein by reference.

BACKGROUND

1. Technical Field

The present disclosure relates to an intraoral scanner, and more particularly, to an intraoral scanner configured to obtain a 3D image of an oral cavity.

2. Background Art

Generally, an impression-taking procedure is performed in a process of diagnosis or treatment of a dental patient. Impression taking is a necessary clinical procedure in establishing a diagnosis and treatment plan for a patient by reflecting conditions of teeth and tissue in an oral cavity in an impression material. In recent years, with application of digital technology to dental clinic and lab processes, the number of cases of using a digital impression in which an oral cavity or an impression body is scanned and converted into digital data without using an impression material in impression taking has increased. In this way, with an increase in the importance of a digital impression in dental diagnosis and treatment, development of technology related to intraoral scanners has been actively carried out.

An intraoral scanner is a device or system inserted into an oral cavity of a dental patient to scan a 3D structure of teeth in a non-contact manner. Generally, recently developed intraoral scanners capture 2D image data of an oral cavity and perform 3D modeling of an oral cavity structure based on the 2D image data. The range of application of intraoral scanners having such functions has expanded among clinical applications, and the intraoral scanners may also be used in fabricating an implant, an orthodontic appliance, and the like in addition to being used in treatment for tooth restoration.

Meanwhile, impression accuracy is important for successful dental treatment. A digital impression using an intraoral scanner does not have a problem of deformation due to contraction, expansion, or the like of an impression material and thus has higher impression accuracy compared to a traditional impression-taking method. However, for an intraoral scanner to be continuously used as a tool for sophisticated dental treatment, there is a need to enhance scanning accuracy. Also, since an intraoral scanner is used by being inserted into an oral cavity of a dental patient in a non-contact manner, it is preferable for the intraoral scanner to have a structure that makes a patient feel comfortable during use of the intraoral scanner.

SUMMARY

Embodiments disclosed in the present specification provide an intraoral scanner having a plurality of optical systems disposed therein to have a structure suitable to be used by being inserted into an oral cavity of a dental patient in a non-contact manner.

One embodiment of the present disclosure provides an intraoral scanner including: a case having an opening part formed at one end thereof; a light source part disposed inside the case and configured to emit light; a first optical system disposed at the opening part and configured to reflect the light emitted from the light source part toward a subject located outside the case; a second optical system disposed adjacent to the first optical system and configured to reflect light reflected from the subject toward the inside of the case; and an image sensor part configured to detect the light reflected by the second optical system.

According to one embodiment, the first optical system may be configured to reflect the light reflected from the subject toward the image sensor part, and the image sensor part may be configured to further detect the light reflected by the first optical system.

According to one embodiment, positions and directions of the first optical system and the second optical system may be set so that a plurality of images of the subject each reflected by the first optical system and the second optical system and detected by the image sensor part do not overlap each other, and each of the images is entirely visible.

According to one embodiment, a dihedral angle between a reflective surface of the first optical system and a reflective surface of the second optical system may be configured to form a minor angle.

According to one embodiment, the second optical system may include a first reflective surface and a second reflective surface configured to reflect the light reflected from the subject toward the inside of the case.

According to one embodiment, the first reflective surface of the second optical system may be adjacent to the reflective surface of the first optical system, and a dihedral angle between the first reflective surface and the reflective surface of the first optical system may be configured to form a minor angle.

According to one embodiment, the second reflective surface of the second optical system may be adjacent to the first reflective surface, and a dihedral angle between the first reflective surface and the second reflective surface may be configured to form a minor angle.

According to one embodiment, the light source part may be configured to emit patterned light or structured light.

According to one embodiment, the image sensor part may be configured to obtain a plurality of stereo images from images of the light reflected from the first optical system and the second optical system.

According to one embodiment, virtual central lines of the light source part, the first optical system, the second optical system, and the image sensor part that are projected on a plane of the case may be arranged to be aligned on a virtual central line projected on the plane of the case.

According to various embodiments of the present disclosure, since a driving part for angle adjustment of each of a plurality of optical systems disposed inside a case of an intraoral scanner is unnecessary, the optical systems can be densely arranged at optimal positions inside the case.

Also, according to various embodiments of the present disclosure, since it is possible to implement an intraoral scanner having a small volume by arranging a plurality of optical systems in a dense structure inside a case, during use of the intraoral scanner, it is not only easy to insert the intraoral scanner into an oral cavity of a dental patient but also easy to move or change a direction of the intraoral scanner in the oral cavity, and thus dental scanning can be precisely performed.

In addition, according to various embodiments of the present disclosure, since two or more stereo images can be obtained from images of light reflected from a plurality of optical systems with only a single image sensor part, manufacturing costs of an intraoral scanner can be reduced, and an internal configuration thereof can be further optimized.

Advantageous effects of the present disclosure are not limited to those mentioned above, and other unmentioned advantageous effects should be clearly understood by those of ordinary skill in the art from the claims below.

DETAILED DESCRIPTION

Figure 1:
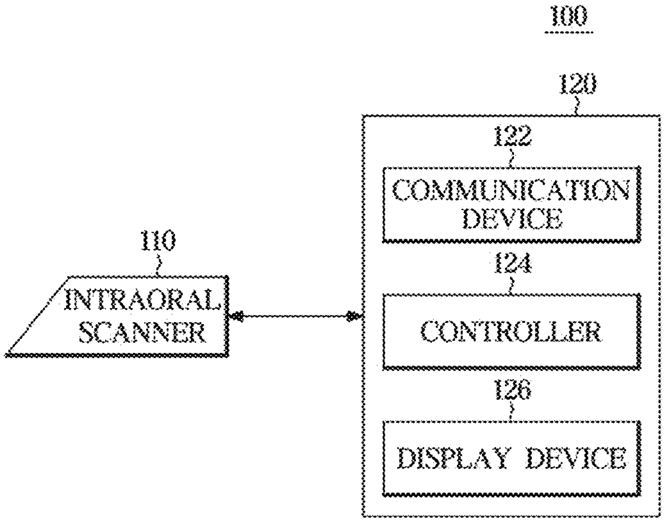
FIG. 1 is a block diagram illustrating a configuration in which an intraoral scanner according to one embodiment of the present disclosure is connected to an intraoral 3D modeling and visualization system.

Hereinafter, details for carrying out the present disclosure will be described in detail with reference to the accompanying drawings. However, in the description below, when there is concern about unnecessarily obscuring the gist of the present disclosure, detailed description of a widely known function or configuration will be omitted.

In the accompanying drawings, the same or corresponding components are denoted by the same reference numerals. Also, in the following description of embodiments, repeated description of the same or corresponding components may be omitted. However, omission of description of a certain component may not mean that the component is not included in a certain embodiment.

Terms used in the present disclosure will be briefly described, and embodiments disclosed herein will be described in detail. General terms that are currently widely used have been selected as terms used herein in consideration of functions in the present disclosure, but the terms may be changed according to an intention or practice of those of ordinary skill in the art, the advent of new technology, and the like. Also, in some cases, some terms may have been arbitrarily selected by the applicant, and in such cases, the meanings of the terms will be described in detail in the corresponding part of the description of the invention. Therefore, the terms used in the present disclosure should be defined based on the meanings of the terms and the content throughout the present disclosure, instead of being simply defined based on the names of the terms.

In the present disclosure, a singular expression includes a plural expression unless the context clearly indicates singularity. Also, a plural expression includes a singular expression unless the context clearly indicates plurality.

In the present disclosure, when a certain part is described as including a certain component, this indicates that the certain part may further include other components instead of excluding other components unless the context clearly indicates otherwise.

In the present disclosure, the upper part of a drawing may be referred to as "upper portion" or "upper side" of a configuration illustrated in the drawing, and the lower part of the drawing may be referred to as "lower portion" or "lower side" of the configuration Also, a portion between the upper portion and the lower portion of the configuration illustrated in the drawing or a remaining portion excluding the upper portion and the lower portion may be referred to as "side portion" or "side surface" of the configuration. The relative terms such as "upper portion" and "upper side" may be used to describe the relationship between configurations illustrated in the drawings, and the present disclosure is not limited by the terms.

In the present disclosure, a direction toward an inner space of one structure may be referred to as "inner side," and a direction protruding to an open outer space may be referred to as "outer side." The relative terms such as "inner side" and "outer side" may be used to describe the relationship between configurations illustrated in the drawings, and the present disclosure is not limited by the terms.

In the present disclosure, the term "A and/or B" refers to A, B, or A and B.

In the present specification, when a certain part is described as being connected to another part, this not only includes a case in which the two parts are directly connected but also includes a case in which the two parts are connected with another configuration disposed therebetween.

Also, terms such as "module" or "part" used in the present disclosure refer to software or hardware components, and a "module" or "part" performs a certain role. However, the meaning of "module" or "part" is not limited to software or hardware. A "module" or "part" may be configured to be present in addressable storage media or configured to replay one or more processors. Therefore, as one example, a "module" or "part" may include at least one of components such as software components, object-oriented software components, class components, and task components, processes, functions, attributes, procedures, subroutines, program code segments, drivers, firmware, micro codes, circuits, data, databases, data structures, tables, arrays, or variables. The components and the "modules" or "parts" and functions provided therein may be combined into a smaller number of components and "modules" or "parts" or may be further separated into a larger number of components and "modules" or "parts."

Advantages and features of the embodiments disclosed herein and methods of achieving the same should become clear from embodiments described in detail below with reference to the accompanying drawings. However, the present disclosure is not limited to the embodiments disclosed below and may be implemented in various different forms. The present embodiments are only provided to make the present disclosure complete and completely inform those of ordinary skill in the art to which the present disclosure pertains of the scope of the invention.

FIG. 1 is a block diagram illustrating a configuration of an intraoral scanning system 100 in which an intraoral scanner 110 according to one embodiment of the present disclosure is connected to an intraoral 3D modeling and visualization server 120. As illustrated, the intraoral scanning system 100 may include the intraoral scanner 110 that can scan a 3D structure of an oral cavity of a dental patient and the intraoral 3D modeling and visualization server 120 connected to the intraoral scanner 110.

For example, the intraoral scanner 110 may be inserted into an oral cavity of a dental patient by a medical worker in a dental clinic to scan teeth in a non-contact manner and capture a plurality of pieces of 2D image data. Also, the intraoral scanner 110 may send the plurality of pieces of captured 2D image data to the 3D modeling and visualization server 120 or may perform 3D oral cavity structure modeling based on the 2D image data by itself.

The intraoral scanner 110 may be connected to the 3D modeling and visualization server 120 through a network configured to communicate via a wire or wirelessly. Here, for example, according to an installation environment, the network may be configured with a wired network such as an electric connection line such as a copper cable, Ethernet, a wired home network (power line communication), a phone line communication device, and RS-serial communication, a wireless network such as a mobile network, a wireless local area network (WLAN), Wi-Fi, Bluetooth, and ZigBee, or a combination thereof.

The intraoral scanner 110 may transmit and receive information and/or data such as 2D image data and 3D oral cavity structure model data to and from the 3D modeling and visualization server 120. The intraoral scanner 110 and the 3D modeling and visualization server 120 may be configured to be physically separated as illustrated, but the present disclosure is not limited thereto. For example, the intraoral scanner 110 and the 3D modeling and visualization server 120 may be integrally configured in a single computing device.

The 3D modeling and visualization server 120 may perform 3D oral cavity structure modeling based on at least two pieces of 2D image data or stereo images obtained from the intraoral scanner 110. In order to perform such functions, the 3D modeling and visualization server 120 may correspond to a computing device including a processor that can perform image processing and 3D modeling (for example, a central processing unit (CPU), a graphics processing unit (GPU), an application processor (AP), a neutral processing unit (NPU), etc.) and a memory that can store 2D image data and 3D oral cavity structure model data. In one embodiment, the 3D modeling and visualization server 120 may include a communication device 122, a controller 124, and a display device 126 as illustrated. The communication device 122 may be configured to transmit and receive information and/or data to and from the intraoral scanner 110. Specifically, the communication device 122 may transmit a command signal of the controller 124 to the intraoral scanner 110 and may receive image information of a target oral cavity structure from the intraoral scanner 110.

The controller 124 may control the intraoral scanner 110 to capture an image of the target oral cavity structure. Specifically, the controller 124 may control at least one or more light source parts (for example, 220 in FIG. 2) installed inside the intraoral scanner 110 to emit light toward at least one of a plurality of optical systems. Also, the controller 124 may control an image sensor part (for example, 250 in FIG. 2) installed inside the intraoral scanner 110 to detect light reflected by at least one of the plurality of optical systems. The controller 124 may control the image sensor part to obtain at least two or more stereo images from an image of the detected light. The controller 124 may control the display device 126 to display the two or more stereo images received from the intraoral scanner 110. Alternatively or additionally, the controller 124 may control 3D oral cavity structure model data calculated based on the two or more stereo images to be visualized and displayed on the display device 126.

The display device 126 may display information and/or data received from the intraoral scanner 110 or the controller 124. In this case, data displayed on the display device 126 may include two stereo images or 3D oral cavity structure model images. In one embodiment, the display device 126 may include a display panel device such as a light emitting diode (LED) display, an organic light emitting diode (OLED) display, a liquid crystal display (LCD), or a touch display.

Figure 2:
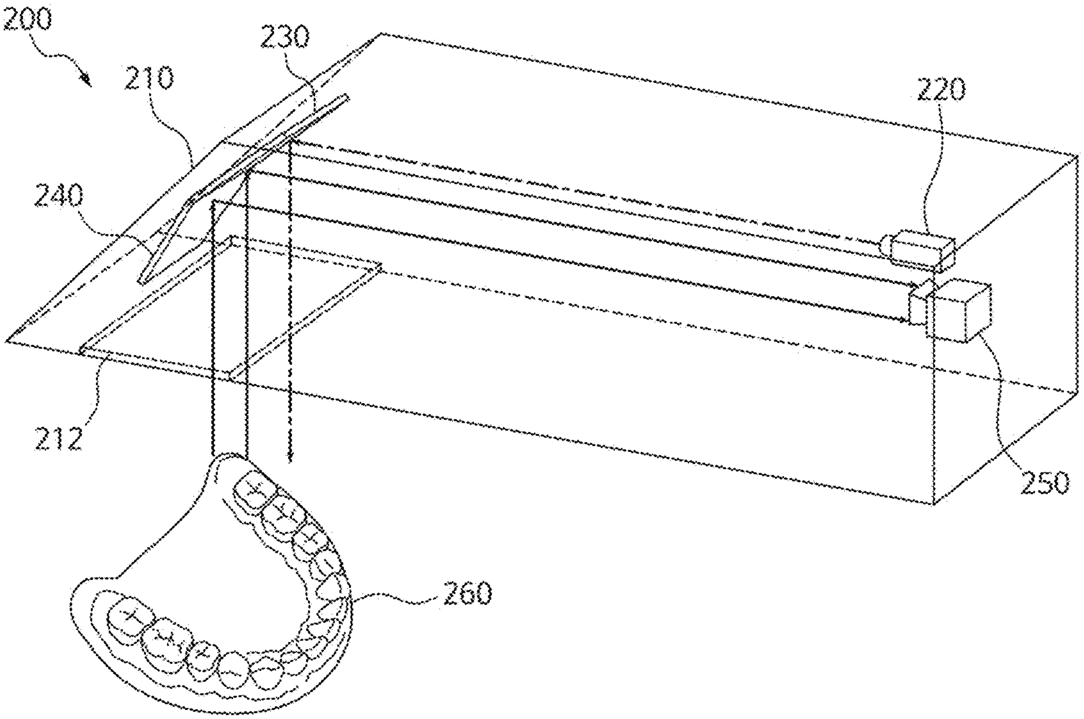
FIG. 2 is a see-through perspective view of the intraoral scanner according to one embodiment of the present disclosure.

FIG. 2 is a see-through perspective view of an intraoral scanner 200 according to one embodiment of the present disclosure. As illustrated in FIG. 2, the intraoral scanner 200 may include a case 210, a light source part 220, a first optical system 230, a second optical system 240, and an image sensor part 250.

The case 210 may be configured to form an exterior of the intraoral scanner 200 and accommodate the light source part 220, the first optical system 230, the second optical system 240, and the image sensor part 250 therein. As illustrated in FIG. 2, the case 210 may have the shape of a trapezoidal box that substantially extends in any one longitudinal direction, but the present disclosure is not limited thereto. For example, the case 210 may have a rectangular parallelepiped shape, a cylindrical shape, a streamlined shape, or any other shape suitable for insertion into an oral cavity.

An opening part 212 may be formed at one end of the case 210. Specifically, the opening part 212 may include an opening formed at one end of the case 210. In this case, the opening of the opening part 212 may be configured to allow light generated or reflected inside the case 210 to be emitted to the outside and external light to be introduced into the case 210. In one embodiment, the opening part 212 may be configured to be positioned at the innermost side of an oral cavity when the intraoral scanner 200 is inserted into the oral cavity.

The light source part 220 may be configured to emit light toward the opening part 212, the first optical system 230, or the second optical system 240. In this case, light emitted from the light source part 220 may correspond to patterned light or structured light. The light may have a linear pattern, a dot pattern, or any other pattern. When patterned light is emitted to a subject 260 such as teeth in an oral cavity located outside the case, deformation of the corresponding pattern may occur according to a 3D structure of a surface of the subject 260. Therefore, the 3D structure of the subject 260 may be identified and modeled based on the deformation of the pattern projected on the surface of the subject 260 or information on changes of positions of feature points.

The light source part 220 may be disposed inside the case 210. Specifically, the light source part 220 may be disposed to be accommodated at the other end inside the case 210 that faces one end of the case 210 at which the opening part 212, the first optical system 230, or the second optical system 240 is formed. For example, the light source part 220 may be disposed to be fixed to an upper portion of the other end inside the case 210.

In one embodiment, the light source part 220 may be disposed at one side end of the case 210, but the present disclosure is not limited thereto. For example, the light source part 220 may be disposed at any intermediate point between one end and the other end of the case 210. That is, the light source part 220 may be disposed at any position inside the case 210 where it is easy for the light source part

220 to emit light toward the opening part 212, the first optical system 230, or the second optical system 240.

The first optical system 230 may be configured to reflect light emitted from the light source part 220 toward the opening part 212. As illustrated in FIG. 2, the first optical system 230 may include at least one reflector. For example, the first optical system 230 may be at least one mirror. In one embodiment, the second optical system 240 may be disposed at the opening part 212 or around the opening part 212. For example, the second optical system 240 may be disposed to be fixed to an inner side surface of the opening part 212. That is, the light emitted from the light source part 220 may be reflected toward the opening part 212 via the reflector of the first optical system 230. Also, the first optical system 230 may be configured to reflect light reflected from the subject 260 toward the inside of the case.

The second optical system 240 may be configured so that light emitted from the reflector of the first optical system 230 causes light reflected by the subject 260 to be reflected toward the inside of the case. The second optical system 240 may include at least one reflector. For example, the second optical system 240 may be at least one mirror. In one embodiment, the second optical system 240 may be disposed adjacent to the first optical system 230 and may be disposed at the opening part 212 or around the opening part 212. For example, as illustrated, the second optical system 240 may be disposed adjacent to a lower portion of the first optical system 230 and may be disposed to be fixed to the inner side surface of the opening part 212.

In one embodiment, a dihedral angle between a reflective surface of the first optical system 230 and a reflective surface of the second optical system 240 may be configured to form a minor angle. Also, positions and directions of the first optical system 230 and the second optical system 240 may be set so that a plurality of images of the subject 260 each reflected by the first optical system 230 and the second optical system 240 and detected by the image sensor part 250 do not overlap each other, and each of the images is entirely visible.

In one embodiment, the light source part 220, the first optical system 230, the second optical system 240, and the image sensor part 250 may be disposed to be axially aligned inside the case 210. For example, virtual central lines of the light source part 220, the first optical system 230, the second optical system 240, and the image sensor part 250 that are projected on a plane of the case may be arranged to be aligned on a virtual central line projected on the plane of the case 210.

In one embodiment, each of the first optical system 230 and the second optical system 240 may be disposed to be fixed to a predetermined position inside the case 210. In this case, a driving part for angle adjustment of the first optical system 230 or the second optical system 240 may not be installed inside the case 210. In this way, since there is no need to arrange another electronic or mechanical component in an area inside the case where the first optical system 230 and the second optical system 240 are disposed, the components inside the case may be densely arranged. Therefore, since it is possible to design an optimal structure of the case 210 from a dense structure of the first optical system 230 and the second optical system 240, it is possible to freely perform a scanning operation in an oral cavity and implement the intraoral scanner 200 with a small volume.

The image sensor part 250 may be configured to detect light reflected or refracted from the first optical system 230 and the second optical system 240. In one embodiment, the image sensor part 250 may be configured to obtain at least two stereo images from light reflected or refracted from each of the first optical system 230 and the second optical system 240. Specifically, the image sensor part 250 may simultaneously obtain at least two images of light reflected by each of the first optical system 230 and the second optical system 240. In this way, since the intraoral scanner 200 includes the first optical system 230 and the second optical system 240 each including at least one reflector, at least two stereo images can be obtained with only the single image sensor part 250. The at least two stereo images obtained by the image sensor part 250 may be used in 3D oral cavity structure modeling performed by a processor afterwards.

In one embodiment, the image sensor part 250 may be disposed at the other end of the case 210. Specifically, the image sensor part 250 may be disposed to be accommodated at the other end inside the case 210 to face the one end of the case 210 where the opening part 212, the first optical system 230, or the second optical system 240 is formed. For example, the image sensor part 250 may be disposed to be fixed to the lower portion inside the case 210 that is adjacent to the light source part 220.

Figure 3:
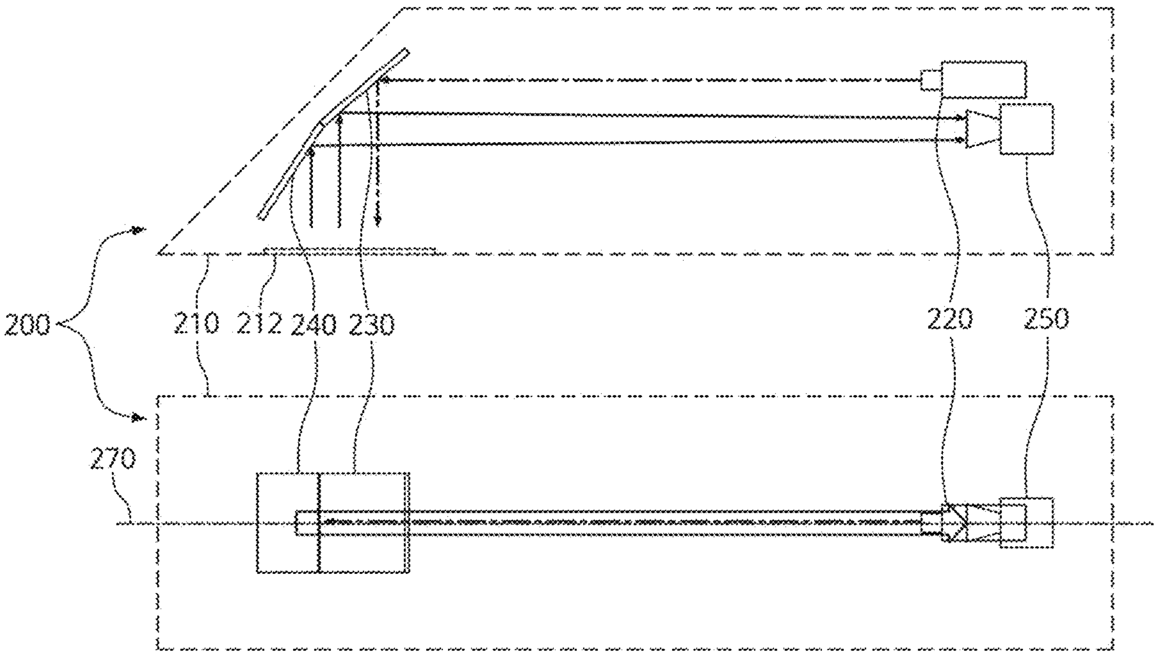
FIG. 3 shows a see-through lateral view and a see-through plan view of the intraoral scanner according to one embodiment of the present disclosure.

FIG. 3 shows a see-through lateral view and a see-through plan view of the intraoral scanner 200 according to one embodiment of the present disclosure. Configurations of FIG. 3 that overlap FIG. 2 will be briefly described based on the embodiment illustrated in FIG. 3. In one embodiment, light may be emitted from the light source part 220 and may be reflected toward the subject located outside the case 210 by the first optical system 230. In this case, light may pass through an opening formed at one side of the opening part 212. Light reflected from the subject may be reflected by the first optical system 230 and the second optical system 240 and emitted toward the image sensor part 250.

In one embodiment, the light source part 220, the first optical system 230, the second optical system 240, and the image sensor part 250 may be disposed to be axially aligned inside the case 210. For example, virtual central lines of the light source part 220, the first optical system 230, the second optical system 240, and the image sensor part 250 that are projected on a plane of the case may be arranged to be aligned on a virtual central line 270 projected on the plane of the case 210. With such a configuration, since it is possible to obtain two or more stereo images from images of light reflected from the plurality of optical systems with only the single image sensor part, manufacturing costs of the intraoral scanner can be reduced, and an internal configuration thereof can be further optimized.

Figure 4:
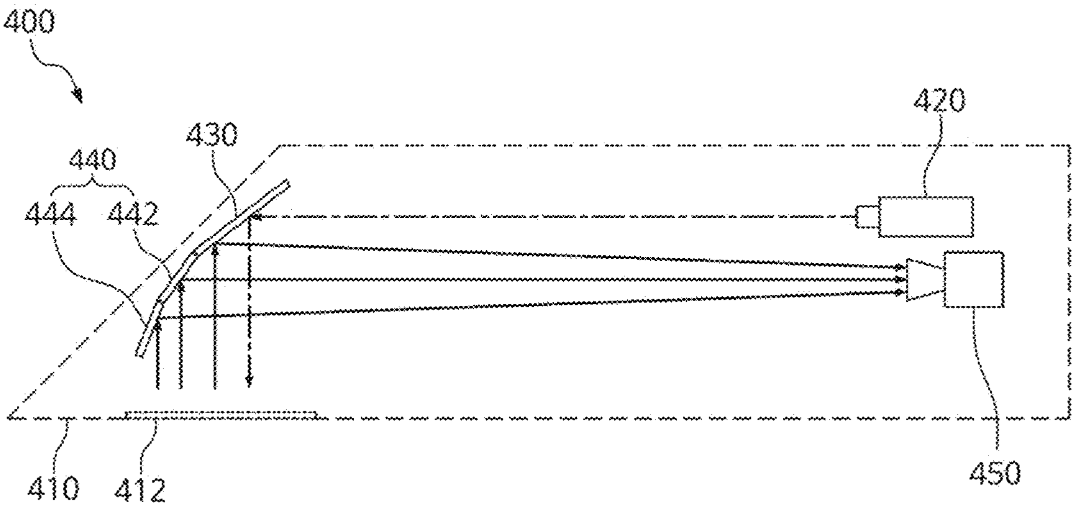
FIG. 4 is a see-through lateral view of an intraoral scanner according to another embodiment of the present disclosure.

FIG. 4 is a see-through lateral view of an intraoral scanner 400 according to another embodiment of the present disclosure. Configurations of FIG. 4 that overlap FIG. 2 will be briefly described based on the embodiment illustrated in FIG. 4. As illustrated in FIG. 4, a light source part 420 may be configured to emit light toward an opening part 412. The light source part 420 may be disposed to be accommodated at the other end inside a case 410 that faces one end of the case 410 at which the opening part 412, a first optical system 430, or a second optical system 440 is formed. For example, the light source part 420 may be disposed to be fixed to a lower portion of the other end inside the case 410.

The first optical system 430 may be configured to reflect light emitted from the light source part 420 toward a subject located outside the case 410. Also, the first optical system 430 may be configured to reflect light reflected by the subject and emitted to the inside of the case 410 toward an image sensor 450. Meanwhile, the second optical system 440 may be configured so that light emitted from a reflector of the first optical system 430 causes light reflected by a subject 470 to be reflected toward the inside of the case. In one embodiment, the second optical system 440 may include at least two reflectors. For example, as illustrated, the second optical system 440 may include a first reflective surface 442 and a second reflective surface 444. In this case, the first reflective surface 442 of the second optical system 440 may be adjacent to a reflective surface of the first optical system 430, and a dihedral angle between the first reflective surface 442 and the reflective surface of the first optical system 430 may be configured to form a minor angle. Also, the second reflective surface 444 of the second optical system 440 may be adjacent to the first reflective surface 442, and a dihedral angle between the first reflective surface 442 and the second reflective surface 444 may be configured to form a minor angle.

Although the first optical system 430 including a single reflector and the second optical system 440 including two reflectors are illustrated in FIG. 4, the number of reflectors included in each optical system is not limited thereto.

Figure 5:
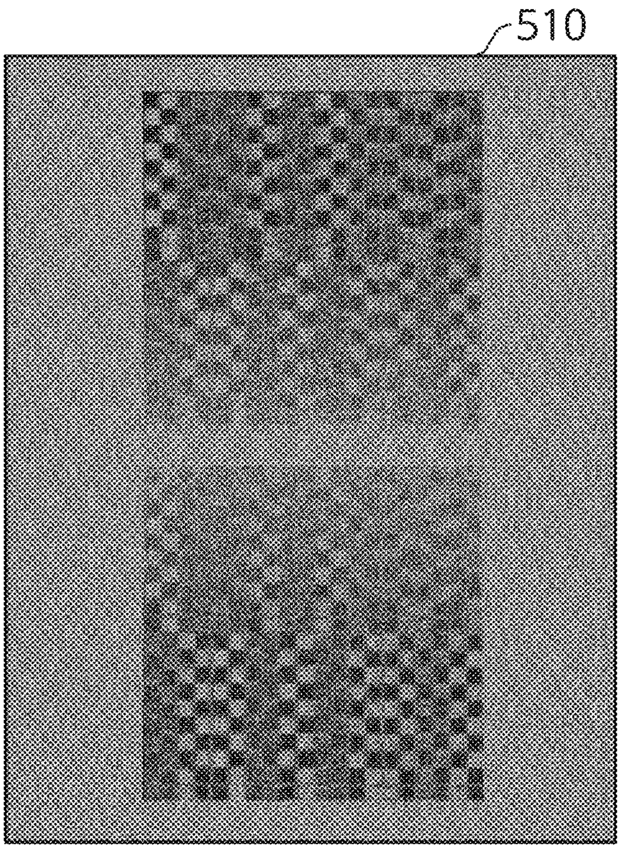
FIG. 5 is a view illustrating examples of stereo images obtained according to one embodiment of the present disclosure.

FIG. 5 is a view illustrating examples of stereo images 510 obtained according to one embodiment of the present disclosure. An image sensor part (for example, 250 in FIG. 2) may be configured to detect light reflected from a first optical system and a second optical system (for example, 230 and 240 in FIG. 2). In one embodiment, the image sensor part may be configured to obtain at least two stereo images 510 from light refracted from the first optical system and the second optical system. Specifically, the image sensor part may simultaneously obtain at least two stereo images of light reflected by at least one reflector of the first optical system and at least one reflector of the second optical system and refracted by a prism. Based on the at least two stereo images obtained in this way, a processor may extract depth data and perform 3D modeling of an oral cavity structure, which is a subject, based on the depth data.

Although an example in which two stereo images are obtained is illustrated in FIG. 5, the present disclosure is not limited thereto, and the image sensor part may be configured to obtain two or more stereo images from light refracted from the first optical system and the second optical system.

The exemplary embodiments of the present invention which have been described above are only disclosed for illustrative purposes. Those of ordinary skill in the art to which the present invention pertains may make various modifications, changes, and additions within the spirit and scope of the present invention, and such modifications, changes, and additions also belong to the scope of the claims.

Since various substitutions, alterations, and changes may be made within the scope not departing from the technical spirit of the present invention by those of ordinary skill in the art to which the present invention pertains, the present invention is not limited by the embodiments described above or the accompanying drawings.

What is claimed is:

1. An intraoral scanner comprising:
- a case having an opening part;
- a light source part disposed inside the case and configured to emit light;
- a first optical system configured to reflect the light emitted from the light source part toward the opening part;
- a second optical system disposed adjacent to the first optical system and configured to reflect light, which is reflected from a subject located outside the opening part, toward the inside of the case; and
- a single image sensor part configured to detect the light reflected by the second optical system;
- wherein the first optical system is configured to reflect the light reflected from the subject toward the single image sensor part; and
- the single image sensor part is configured to further detect the light reflected by the first optical system.

2. The intraoral scanner of claim 1, wherein positions and directions of the first optical system and the second optical system are set so that a plurality of images of the subject each reflected by the first optical system and the second optical system and detected by the single image sensor part do not overlap each other, and each of the images is entirely visible.

3. The intraoral scanner of claim 1, wherein a dihedral angle between a reflective surface of the first optical system and a reflective surface of the second optical system is configured to form a minor angle.

4. The intraoral scanner of claim 1, wherein the second optical system includes a first reflective surface and a second reflective surface configured to reflect the light reflected from the subject toward the inside of the case.

5. The intraoral scanner of claim 4, wherein the first reflective surface of the second optical system is adjacent to the reflective surface of the first optical system, and a dihedral angle between the first reflective surface and the reflective surface of the first optical system is configured to form a minor angle.

6. The intraoral scanner of claim 4, wherein the second reflective surface of the second optical system is adjacent to the first reflective surface, and a dihedral angle between the first reflective surface and the second reflective surface is configured to form a minor angle.

7. The intraoral scanner of claim 1, wherein the light source part is configured to emit patterned light or structured light.

8. The intraoral scanner of claim 1, wherein the single image sensor part is configured to obtain a plurality of stereo images from images of the light reflected from the first optical system and the second optical system.

9. The intraoral scanner of claim 1, wherein virtual central lines of the light source part, the first optical system, the second optical system, and the single image sensor part that are projected on a plane of the case are arranged to be aligned on a virtual central line projected on the plane of the case.

* * * * *